(12) United States Patent
Berstein (10) Patent No.: US 7,261,697 B2
(45) Date of Patent: Aug. 28, 2007

(54) APPARATUS FOR DETERMINATION OF STROKE VOLUME USING THE BRACHIAL ARTERY

(76) Inventor: Donald P. Berstein, P.O. Box 523, Rancho Santa Fe, CA (US) 92067

( * ) Notice: Subject to any disclaimer, the term of this patent is extended or adjusted under 35 U.S.C. 154(b) by 260 days.

(21) Appl. No.: 10/870,281

(22) Filed: Jun. 16, 2004

(65) Prior Publication Data

US 2005/0283088 A1    Dec. 22, 2005

(51) Int. Cl.
A61B 5/04    (2006.01)
(52) U.S. Cl. .................. 600/506; 600/513; 600/536
(58) Field of Classification Search ............... 600/506, 600/526
See application file for complete search history.

(56) References Cited

U.S. PATENT DOCUMENTS

| | | |
|---|---|---|
| 3,340,867 A | 9/1967 | Kubicek et al. |
| 4,450,527 A | 5/1984 | Sramek |
| 4,562,843 A | 1/1986 | Djordjevich et al. |
| 4,676,253 A * | 6/1987 | Newman et al. ............ 600/506 |
| 4,807,638 A | 2/1989 | Sramek |
| 4,836,214 A | 6/1989 | Sramek |
| 4,953,556 A | 9/1990 | Evans |
| 5,103,828 A | 4/1992 | Sramek |
| 5,178,154 A | 1/1993 | Ackmann et al. |
| 5,309,917 A | 5/1994 | Wang et al. |
| 5,316,004 A | 5/1994 | Chesney et al. |
| 5,423,326 A | 6/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,685,316 A | 11/1997 | Schookin et al. |
| 5,782,774 A | 7/1998 | Shmulewitz |
| 5,791,349 A | 8/1998 | Shmulewitz |
| 6,016,445 A | 1/2000 | Baura |
| 6,058,325 A | 5/2000 | Baura |
| 6,095,987 A | 8/2000 | Shmulewitz et al. |
| 6,102,869 A | 8/2000 | Meier et al. |
| 6,161,038 A | 12/2000 | Schookin et al. |
| 6,186,955 B1 | 2/2001 | Baura |
| 6,511,438 B2 | 1/2003 | Bernstein et al. |
| 6,561,986 B2 | 5/2003 | Baura et al. |
| 6,602,201 B1 | 8/2003 | Hepp et al. |
| 6,636,754 B1 | 10/2003 | Baura et al. |

(Continued)

Primary Examiner—Carl Layno
Assistant Examiner—Tammie K. Heller
(74) Attorney, Agent, or Firm—DLA Piper US LLP (57) ABSTRACT

Provided herein are methods and apparatus for stroke volume determination by bioimpedance from a patient's upper arm, or brachium, utilizing pulsations of the brachial artery contained therein. The apparatus includes two or more spaced apart alternating current flow electrodes positioned on the patient's arm proximate the brachial artery and two or more spaced apart voltage sensing electrodes positioned on the patient's arm proximate the brachial artery. The voltage sensing electrodes are positioned between the alternating current flow electrodes on the arm. An alternating current source is electrically connected to the alternating current flow electrodes and a voltmeter electrically is connected to the voltage sensing electrodes. A data input device is provided along with a processing unit in communication with the data input device, the alternating current source, alternating current flow electrodes, the voltmeter, and voltage sensing electrodes. The processing unit is capable of using data from the data input device and voltage sensing electrodes to calculate the stroke volume of the patient.

8 Claims, 4 Drawing Sheets

U.S. PATENT DOCUMENTS 6,829,501 B2    12/2004  Nielsen et al.
2002/0193689 A1*  12/2002  Bernstein et al. ........... 600/454
2003/0163058 A1*  8/2003  Osypka et al. .............. 600/513

* cited by examiner

APPARATUS FOR DETERMINATION OF STROKE VOLUME USING THE BRACHIAL ARTERY

BACKGROUND OF THE INVENTION

1. Field of the Invention

This present invention relates to the determination of the volumetric output of the left ventricle of a person's heart per beat, known as stroke volume (SV) (mL), and, the volumetric output of a person's heart per minute, otherwise known as the cardiac output (CO) (L/Min). More particularly, this invention relates to the determination of SV and CO by transbrachial electrical bioimpedance.

2. Background Information

All methods, apparatus and inventions related to the measurement of SV/CO by the electrical bioimpedance method have heretofore been implemented either by the transthoracic method, also known as transthoracic or thoracic electrical bioimpedance plethysmography (or cardiography), or by total body (whole body) electrical bioimpedance plethysmography, also known as wholebody electrical bioimpedance cardiography (Moshkovitz Y, et al. Curr Opin Cardiol 2004; 19:229-237). Apart from a velocimetric method and apparatus described by Bernstein et al. (U.S. Pat. No. 6,511,438 B2), all prior art assumes a plethysmographic origin for the measured impedance change with respect to time ($\Delta Z(t)$), and its peak rate of change ($dZ/dt_{max}$), coinciding with each beat of the heart (Moshkovitz Y, et al. Curr Opin Cardiol 2004; 19:229-237). The plethysmograhic-based transthoracic SV equations used clinically basically comprise two methods; they are described in U.S. Pat. No. 6,511,438 B2, and are known as the Nyboer-Kubicek equation (Kubicek equation) and the Sramek-Bernstein equation. The deficiencies of the method and apparatus invented by Bernstein et al., disclosed in U.S. Pat. No. 6,511,438 B2, include the following:

1. A volume conductor, $V_c$, which underestimates the intrathoracic blood volume (ITBV) by approximately 15-20%
2. The implementation of a square root function for heart rate (H.R.) frequency (i.e. $\sqrt{f_0} = 1/(T_{RR})^{0.5} = (H.R./60)^{0.5}$) which is superfluous and unnecessary.
3. A best method in the preferred embodiment for determining left ventricular ejection time, $T_{lve}$, is not disclosed.
4. A best method in the preferred embodiment for determining point B is not disclosed
5. A best method in the preferred embodiment for determining $dZ/dt_{max}$, based on the accurate determination of point B, is not disclosed There are numerous drawbacks to the current methods and apparatus used for measurement of the transthoracic electrical bioimpedance stroke volume parameters. What is needed is an alternative approach to the transthoracic electrical bioimpedance determination of stroke volume; specifically, an alternative site for signal acquisition, and better methods to measure the independent variables comprising the stroke volume equation.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein identical reference numerals designate the same components. The invention may be better understood by reference to one or more of these drawings in combination with the description presented herein. It should be noted that the features illustrated in the drawings are not necessarily drawn to scale.

FIG. 1 shows placement of electrodes on a patient. A.C.(I) is injected through a segment of the upper arm, otherwise known as the brachium, the boundaries of which are the deltoid muscles of the shoulder and axilla proximally, and the elbow and antecubital fossa distally. Embedded within the brachial musculature and connective tissue, and anatomically situated medial to the brachial bone, otherwise known as the humerus, is the brachial artery. The upper arm, including the connective tissue, bone, nervous tissue, veins, and the brachial artery comprise an impedance (Z) to current flow. The passage of A.C across the brachium generates a quasi-static voltage, ($U_0$), and, concordant with every pressure pulse of the brachial artery, a time-dependent drop in voltage, ($\Delta U(t)$), this pressure pulse following every onset of left ventricular ejection with a short time delay.

FIG. 3a further shows an example where points B and X are apparent on the $dZ/dt$ curve and FIG. 3b shows an example where point B is not detectable, but point X is detectable on the $dZ/dt$ curve.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention discloses a method and apparatus for the determination of stroke volume (SV) and cardiac output (CO) by transbrachial electrical bioimpedance, wherein the signal source is the brachial artery. SV and CO, while not sensitive indices of the overall intrinsic force generation capacity, or contractility of the heart muscle, are the best indicators of the overall performance of the heart considered as a muscular pump. The apparatus and method disclosed involve the application of a constant magnitude alternating current of high frequency and small amplitude across a segment of a person's upper extremity, and more specifically, the upper arm, otherwise known as the brachium. The present invention may also provide for calibrating the transbrachial method and apparatus by determining SV/CO from the transthoracic approach. Thus, in contradistinction to the generally accepted transthoracic bioimpedance method for SV/CO determination, the present invention relates to the acquisition and signal processing of the cardiogenically-induced, pulsatile transbrachial bioimpedance signal for the purpose of SV/CO determination.

Advantages of the transbrachial method include:
1. Stroke volume (SV) and cardiac output (CO) values are not affected by excess, extra-vascular, intrathoracic liquids; namely, pulmonary edema fluid.
2. Baseline transbrachial quasi-static impedance, $Z_0$, is not affected by pulmonary (lung) ventilation, thereby obviating the necessity for sophisticated stabilizing adaptive filtering techniques to obtain a steady baseline for measurement of the cardiac-induced transbrachial impedance change, $\Delta Z(t)$, and the magnitudes and fiducial landmarks on its first time-derivative, transbrachial dZ/dt.
3. The cumbersome and user-unfriendly transthoracic band, or tetrapolar spot-electrode array, is replaced by a circumferential or non-circumferential arm band or bands, an adhesive strip or other appropriate means for positioning the electrodes near the brachial artery containing a bipolar, or alternatively, a tetrapolar spot (or band) electrode array positioned on the medial aspect of the brachium between the axilla (arm pit) and a point distal on the brachium at the level of the olecranon process (elbow).
4. With the arm at rest, motion artifacts are minimized as compared to the transthoracic approach, and thus, adaptive filtering techniques are less critical.
5. Long-term monitoring of SV/CO in the surgical operating room, or intensive care unit, is facilitated by application of the apparatus to the arm, containing the bipolar, or, alternatively, the tetrapolar montage.
6. The bioimpedance signal obtained from the brachium is unaffected by the presence of chest thoracostomy tubes, external pacemaker wires, surgical bandages or appliances, and percutaneously placed central venous access catheters located in the neck or upper chest.
7. Without the perturbing influence of pulmonary ventilation, and pulmonary artery and other intrathoracic large vessel venous pulsations, the signal to noise ratio (S/N) relating to that portion the transbrachial dZ/dt signal pertaining only to left ventricular ejection is substantially higher than that of the transthoracic approach.

As disclosed above, the present invention relates to the measurement of stroke volume (SV) and cardiac output (CO) from the transbrachial method, using the brachial artery as the cardiogenically-induced signal source. Methodologically, the transbrachial method is similar to the transthoracic technique for determining SV. However, in the transthoracic technique, signal acquisition is effected over a segment of thorax by placement of voltage sensing electrodes at the base of the neck, bilaterally, and lower thorax at the xiphoid level, bilaterally. In contrast, the transbrachial technique uses a segment of brachium between voltage sensing electrodes positioned proximate the axilla (arm pit) and junction of the upper and lower arm at the level of the olecranon process of the elbow. (see FIG. 1).

Figure 1:
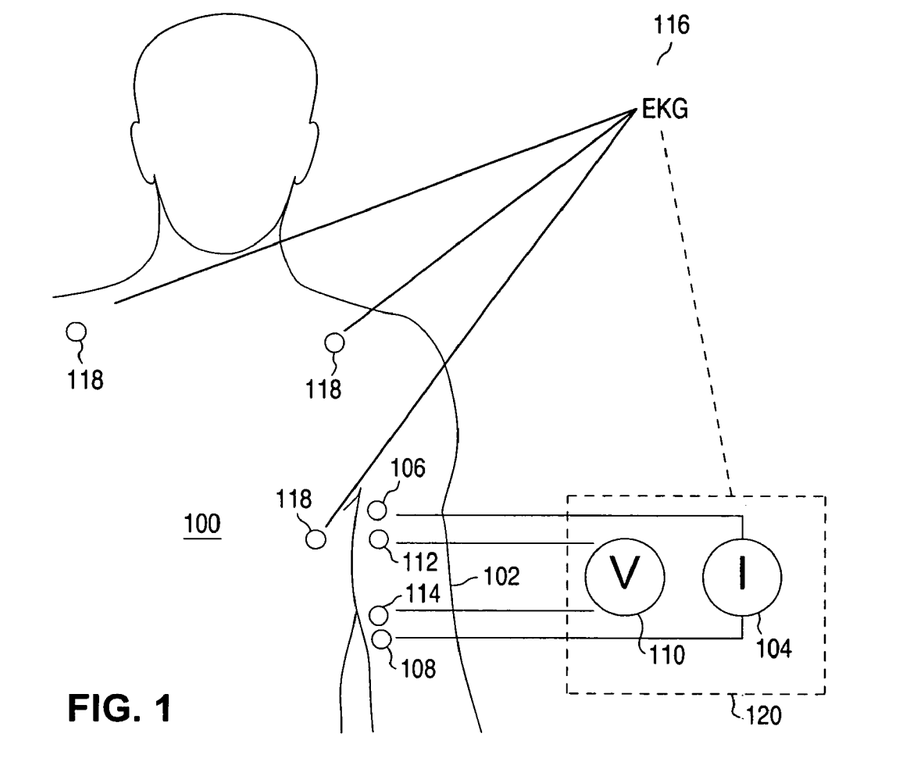

FIG. 1 schematically shows one apparatus embodiment according to the present invention, and its electrical interface with a subject 100. Signal acquisition from the upper arm 102 (brachium) requires application of a constant magnitude alternating current (A.C.) 104 of high frequency and small amplitude to electrodes 106, 108 that are spaced apart, with one or more electrodes affixed to the skin of the axilla, as well as one or more electrodes placed medially at the level of the antecubital fossa creating a current field. In this embodiment, the electrodes are applied to the subject's left arm. In other embodiments, the electrodes may be positioned on the right arm.

With the current field thus generated, the potential difference between the current injecting electrodes or alternating current flow electrodes 106, 108 is measured by a voltmeter 110 connected to the voltage sensing electrodes 112, 114 placed within the current field (see FIG. 1). A baseline impedance between the voltage sensing electrodes 112, 114, as well as a change in impedance, $\Delta Z(t)$ can be measured transbrachially. When the $\Delta Z(t)$ signal is electronically differentiated, $dZ/d_{(brachium)}$ results, its peak systolic magnitude being $dZ/dt_{max(brachium)}$. Many different methods of applying the electrodes or electrode arrays to the arm are envisioned, such as spot electrodes, arm band(s) both circumferential and non-circumferential, adhesive strips or other attachment means known in the art. In one embodiment, an 8 spot-electrode array can be implemented. Alternatively, in another embodiment, a 4 spot-electrode array, placed on the inner, or medial aspect of the upper arm, proximate the brachial artery, can be implemented. Alternatively, 4 non-circumferential band (strip) electrodes, embedded in an adhesive carrier, may be affixed to the brachium, medially, and used in lieu of spot electrodes.

The voltages measured by the Voltmeter 110 not only contains a signal caused by the AC applied, but may also contain a signal component from which an electrocardiogram (ECG) can be derived. The application of filters separates the AC related and ECG related signal components. In another embodiment, EKG 116 may also be measured by placing EKG electrodes 118 on the patient 100. In the figure, a 3-lead EKG is shown and EKG is measured by known means. The magnitude of the alternating current (A.C.) 104 and voltmeter 110 may be components of an apparatus 120. The apparatus 120 may also include an input device and a processor. The input device may be any suitable device that provides information to the apparatus, such as a keyboard. The input device may also receive information from external sources, such as the EKG 116. The processor is in communication with the data input device, the alternating current source 104 and electrodes 106, 108, and the voltmeter 110 and electrodes 112, 114. The processor is capable of receiving the information and calculating the stroke volume and cardiac output of the patient 100. The stroke volume and cardiac output of the patient may be displayed on a screen or be sent to other devices via a data output device of the apparatus.

Figure 2:
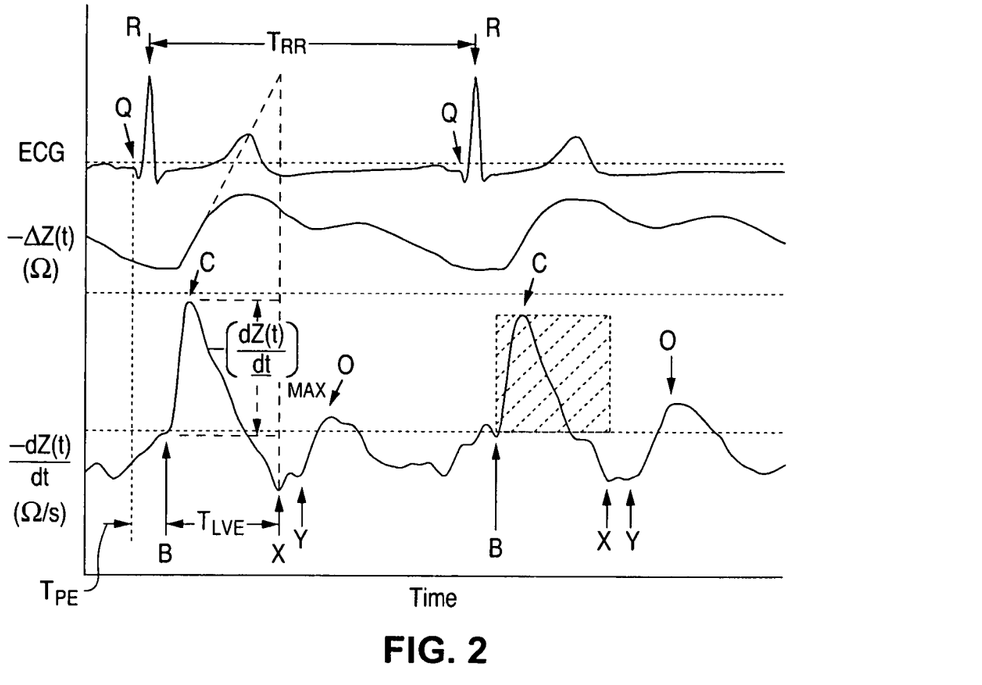
FIG. 2 shows an example of ECG, $\Delta Z(t)$ and $dZ/dt$ waveforms obtained transthoracically from a human subject, where $T_{RR}$=the R-R interval, or the time for one cardiac cycle; Q=onset of ventricular depolarization; . . . =maximum systolic upslope extrapolation of $\Delta Z(t)$; B=aortic valve opening; C=peak rate of change of the thoracic cardiogenic impedance variation, $dZ/dt_{max}$; X=aortic valve closure; Y=pulmonic valve closure; O=rapid ventricular filling wave; Q-B interval=pre-ejection period, $T_{PE}$; B-C interval=time-to-peak $dZ/dt$, TTP; B-X interval=left ventricular ejection period, $T_{LVE}$. $dZ/dt$ waveform to the right shows $dZ/dt_{max}$ remaining constant throughout the ejection interval, $T_{LVE}$, which represents outflow compensation.

FIG. 2 shows an example of ECG, $\Delta Z(t)$ and $dZ/dt$ waveforms from a human subject 100, where $T_{RR}$=the R-R interval, or the time for one cardiac cycle; Q=onset of ventricular depolarization; . . . =maximum systolic upslope extrapolation of $\Delta Z(t)$; B=aortic valve opening; C=peak rate of change of the thoracic cardiogenic impedance variation, $dZ/dt_{max}$; X=aortic valve closure; Y=pulmonic valve closure; O=rapid ventricular filling wave; Q-B interval=pre-ejection period, $T_{PE}$; B-C interval=time-to-peak dZ/dt, TTP; B-X interval=left ventricular ejection period, $T_{LVE}$. dZ/dt waveform to the right shows $dZ/dt_{max}$ remaining constant throughout the ejection interval, $T_{LVE}$.

Rationale for use of the brachium as an appropriate anatomic site for SV measurement by the bioimpedance technique is as follows. When A.C. (I) is injected through a segment of upper arm, otherwise known as the brachium, the boundaries of which are the deltoid muscles of the shoulder and axilla, proximally, and the elbow and antecubital fossa, distally, a quasi-static voltage, $U_0$, and voltage change, $\Delta U(t)$, can be measured between the current injecting electrodes. Embedded within the brachial musculature and connective tissue, and anatomically situated medial to the brachial bone, otherwise known as the humerus, is the brachial artery. The brachial artery is a large artery, continuous with both the subclavian and axillary arteries, and, whereas the left subclavian artery is a major branch of the arch of the thoracic aorta, the right subclavian artery is a branch of the innominate artery. The contents of the upper arm, including connective tissue, bone, nervous tissue, veins, and the brachial artery, comprise an impedance (Z) to current flow. The passage of A.C. across the brachium generates a quasi-static voltage, $U_0$, and, concordant with every pressure pulse of the brachial artery, a time-dependent drop in measured transbrachial voltage, $\Delta U(t)$, this following shortly after the onset of left ventricular ejection. The magnitude of the time delay ($\Delta t$, ms) between the brachial artery pressure pulse and the onset of left ventricular ejection is a function of pulse wave velocity. Transthoracically, the peak rate of change of impedance, $dZ/dt_{max}$, resulting from electronic differentiation of $\Delta Z(t)$, corresponds in time with peak aortic blood acceleration, $dv/dt_{max}$ (cm/s$^2$). Thus, in the preferred embodiment of the invention, $dZ/dt_{max(brachial)}$ represents the ohmic analog of peak blood acceleration in the brachial artery. Chemla et al. (Fundam Clin Pharmacol 1996; 10:393-399) showed that the measured acceleration of blood in the brachial artery is highly correlated (r=0.79) and linearly proportional with blood acceleration in the ascending aorta. Moreover, whereas the magnitude of brachial artery blood velocity is affected by downstream peripheral vasoactivity (vasodilation, vasoconstriction), the magnitude of brachial artery blood acceleration is modulated only by beta ($\beta$) adrenergic stimulation or depression of the cardiac adrenoceptors (Chemla D, et al. Am J Cardiol 1990; 65:494-500). As extrapolated from Visser (Ann Biomed Eng 1989; 17:463-463), when flowing blood is interrogated by a field of alternating current (A.C.), the acceleration of blood in the aorta is measured as the aortic reduced average blood acceleration which is the mean aortic acceleration divided by the vessel radius: $(dv/dt_{(mean)}/R)$. When $[(dv/dt_{(mean)}/R]_{max}$, or peak aortic reduced average blood acceleration (1/s$^2$), undergoes square root transformation, peak aortic reduced average blood velocity (1/s) results. Likewise, when $dZ/dt_{max}/Z_0$ (1/s$^2$) undergoes square root transformation, ohmic mean velocity results, $\Delta Z_v(t)_{max}/Z_0$ (1/s). Because of the high correlation of $dv/dt_{max}$ measured in the aorta, with that of the brachial artery, it is claimed by the present invention that SV can also be obtained from the brachial artery. Thus, $$SV_{(brachium)} = V_{c(brachium)} \cdot \sqrt{[(dZ/dt_{max})/Z_0]_{(brachium)}} \cdot T_{lve}. \qquad \text{equation 1}$$

where:

$V_{c(brachium)}$ equals the volume conductor, or volume of electrically participating brachial tissue (mL);

$dZ/dt_{max}$ equals the peak rate of change (peak first time-derivative) of the measured cardiogenically induced transbrachial impedance variation ($\Omega/s^2$);

$Z_0$ equals the quasi-static transbrachial base impedance (Ohm, $\Omega$);

and $T_{lve}$ equals left ventricular ejection time (s).

In one embodiment:

$$V_{c(brachium)} = C_1 \cdot [W \cdot C_2];$$

$$C_2 = C_3/(BMI_n)^y$$

$$BMI_n = BMI_p/C_4$$

a. W=weight in kilograms (kg);-
b. $40 \leq C_3 \leq 100$ (mL/kg), wherein $C_3$ in the preferred embodiment=70 mL/kg;
c. $BMI_n$=normalized body mass index (dimensionless), wherein $0.4 \leq BMI_n < 4.0$, wherein the preferred embodiment, $BMI_n=1$
d. $BMI_p$=a person's body mass index=Weight(kg)/Height (meters)$^2$ (kg/m$^2$)
e. $15 \leq C_4 \leq 40$ kg/m$^2$, wherein $C_4=24$ kg/m$^2$ in the preferred embodiment.
f. $0.2 > y > 0.8$, wherein y=0.5 in the preferred embodiment.
g. $0 > C_1 \leq 50,000$, wherein $C_1$ is proprietary in the preferred embodiment Unlike previously described bioimpedance techniques, which broadly assume a plethysmographic or volumetric origin for the cardiogenic impedance change, $\Delta Z(t)$, and its peak first time derivative, $dZ(t)/dt_{max}$, the present technique assumes $dZ(t)/dt_{max}$ to represent the ohmic equivalent of the peak acceleration of red blood cells. Thus, when the first time-derivative of $\Delta Z(t)$ is taken, $dZ/dt$, its peak magnitude, $dZ/dt_{max}$, can be shown to coincide in time with the peak acceleration of blood flow, $dv/dt_{max}$ (cm/s$^2$), and not with the peak rate of change of volume, $dV/dt_{max}$ (mL/s). Consequently, to obtain ohmic mean velocity, $dZ/dt_{max}/Z_0$ (1/s$^2$) must undergo square root transformation. This transformation is to be known as Root Mean Square Acceleration Step-down Transformation: $\sqrt{[(dZ/dt_{max})/Z_0]}$ (1/s). It thus follows that, brachial artery $dZ/dt_{max}/Z_0$ is analogous to peak brachial reduced average blood acceleration. To obtain brachial artery ohmic mean velocity, the transformation is likewise implemented. Thus, the signal processing technique, comprising part of the invention, implies that the proper designation for the transbrachial approach is correctly stated as Transbrachial Electrical Bioimpedance Cardiovelocimetry or, simply, Transbrachial bioimpedance velocimetry.

Impedance Measurement Techniques in the Preferred Embodiment of the Invention

Figure 3A:
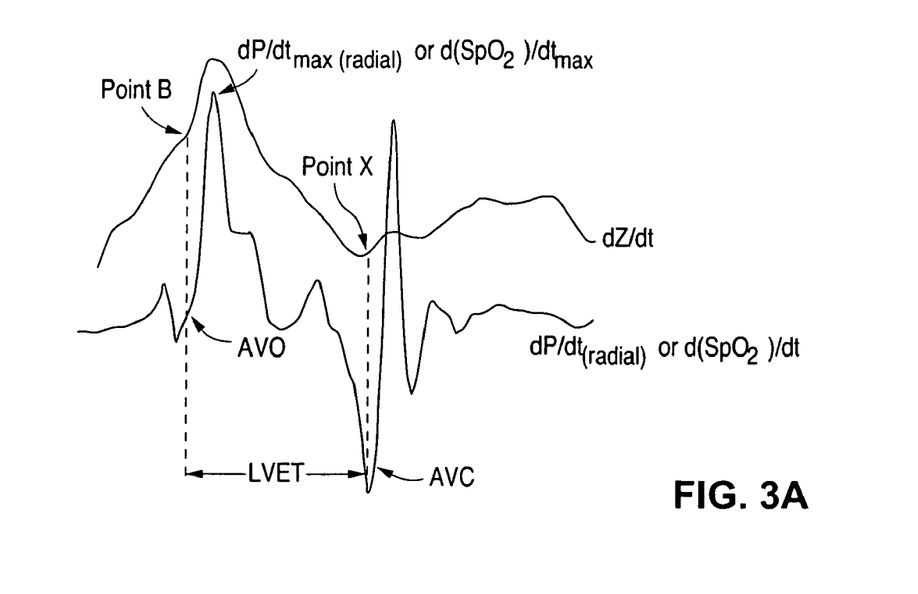
FIGS. 3a and 3b show the relationship between the $dZ/dt$ curve and the $dP/dt$ or $d(SpO_2)/dt$ curve.
Figure 3B:
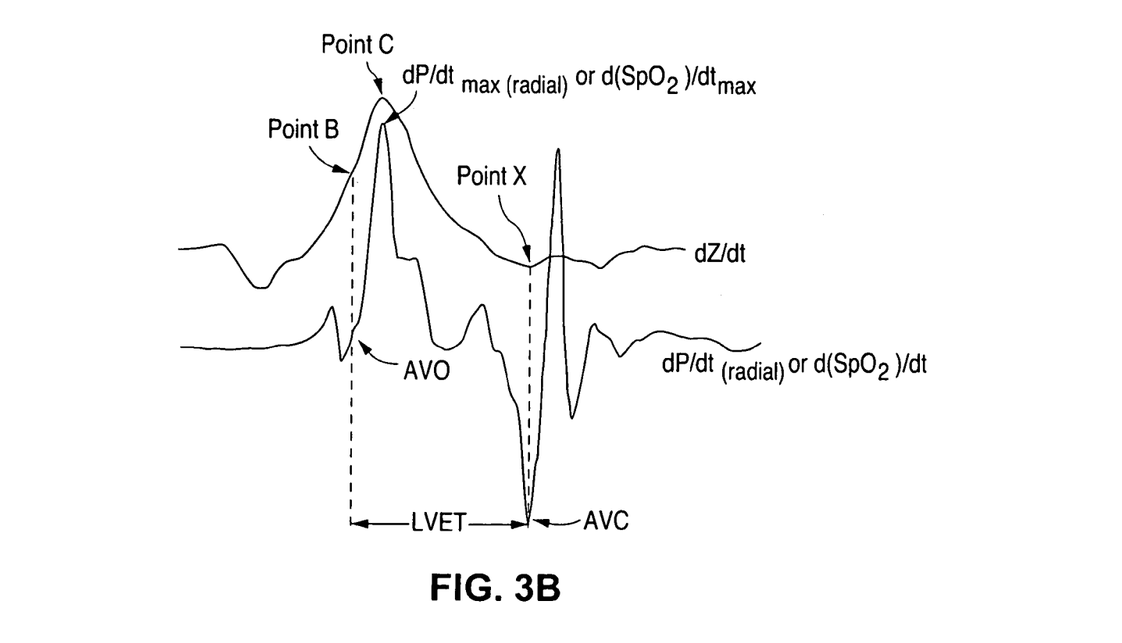

FIGS. 3a and 3b show the relationship between the $dZ/dt$ curve and either the $dP/dt$ or $d(SpO_2)/dt$ curves. FIG. 3a further shows an example where points B and X are apparent on the $dZ/dt$ curve and FIG. 3b shows an example where point B is not detectable, but point X is detectable on the $dZ/dt$ curve. Thus, determination of left ventricular ejection time, ($T_{lve}$), onset of flow(point B), and the ohmic equivalent of peak brachial artery reduced average blood acceleration, ($dZ/dt_{max}/Z_{0\ (brachium)}$), while ideally measured directly from the $dZ/dt$ curve, are supplemented obligatorily by alternative means. The said alternative/obligatory means for determining $T_{lve}$ are those obtained from means such as from the waveform corresponding to the photoplethysmographic pulse oximetry waveform, $\Delta SpO_2(t)$, or its first time-derivative, $d(SpO_2)/dt$, and/or by the waveform obtained from a non-invasive applanated radial arterial pressure pulse waveform, $\Delta P(t)_{(radial)}$, or its first time-derivative, $dP/dt_{(radial)}$. (see FIG. 4)

The said means for determining point B on the transbrachial $dZ/dt$ curve are those methods used for determining $T_{lve}$ when point X on the transbrachial $dZ/dt$ curve, or its first time derivative ($d^2Z/dt^2$), are identifiable by those skilled in the art of bioimpedance curve analysis. When point X is not identifiable on the transbrachial $dZ/dt$ curve, or its first time-derivative, $d^2Z/dt^2$, then alternative means for point B detection are necessary. In the absence of an identifiable point X by those skilled in the art of $dZ/dt$ curve analysis, said means for point B detection include use of the first time-derivative of the applanated radial pressure waveform tracing, $dP/dt$(radial). It will be clear to those skilled in the art of curve analysis, why the aforementioned said means are superior to those disclosed by others, and most recently by Baura et al. (U.S Pat. No. 6,561,986 B2).

Methods for Determination of Left Ventricular Ejection Time ($T_{lve}$, LVET):

1. $dZ/dt$ waveform analysis: $T_{lve}$ (LVET) measured across the brachium is defined as the temporal interval from point B, which occurs shortly after aortic valve opening (AVO), albeit with a time delay, to point X, which coincides in time, albeit with a short time delay, to aortic valve closure (AVC), these time delays dictated by pulse wave velocity.
2. Pulse Oximetry waveform ($\Delta SpO_2(t)$): LVET is defined as the temporal interval (seconds) from the onset of the oximetric pulse as zero baseline, signifying the onset of ejection, albeit with a time delay, to the oximetry wave equivalent of the dicrotic notch, which signifies aortic valve closure, albeit with a time delay, and the end of ejection. The oximetry waveform can be obtained from any appropriate site on, or within the human body, but, in the preferred embodiment, the distal digit of the human finger is deemed most appropriate.
3. Applanation Tonometry Pressure Pulse waveform ($\Delta P(t)_{(radial)}$): LVET is defined as the temporal interval (seconds) from the onset of the pressure pulse at zero baseline, signifying the onset of ejection, albeit with a time delay, to the dicrotic notch equivalent, which signifies aortic valve closure, albeit with a time delay, and the end of ejection. In the preferred embodiment, the pressure pulse waveform is obtained from the radial artery at the wrist, but may be obtained from any site on the arm, specifically from either brachial artery.
4. Regression Equations for $T_{lve}$ versus Heart Rate (HR): LVET is determined by Weissler's regression equations: Male: $T_{lve}=-0.0017\cdot HR+0.413$; Female: $T_{lve}=-0.0016\cdot HR+0.418$.

With exemplary $dZ/dt$ waveforms, such as those shown in FIG. 3a, point B and point X are readily distinguishable by one skilled in the art of curve analysis. However, these fiducial landmarks are frequently distorted by motion and ventilation artifacts (especially using the transthoracic approach), as well as by certain disease processes. LVET may be more accurately measured by curve analysis of the pulse oximetry and applanation tonometry waveforms (FIG. 3b), or their first time-derivatives. In one embodiment of the invention, either or both methods may be implemented. Of these techniques, applanation tonometry is most likely to demonstrate a dicrotic notch, and, therefore, is considered the preferred technique. Furthermore, for those skilled in the art of computer waveform analysis, the points coinciding with the beginning and end of ejection can be readily identified from the first time-derivative curves of both the oximetry and applanation tonometry waveforms; namely, $d(SpO_2)/dt$ and $dP/dt_{(radial)}$. In the preferred embodiment, the best method constitutes computer analysis of the first time-derivatives. In another embodiment, regression equations for heart rate versus LVET may be implemented.

Methods for point B detection on the $dZ/dt$ waveform:
1. Methods for determining point B when point X is readily identifiable by one skilled in the art of curve analysis (see FIG. 3a).

Figure 4:
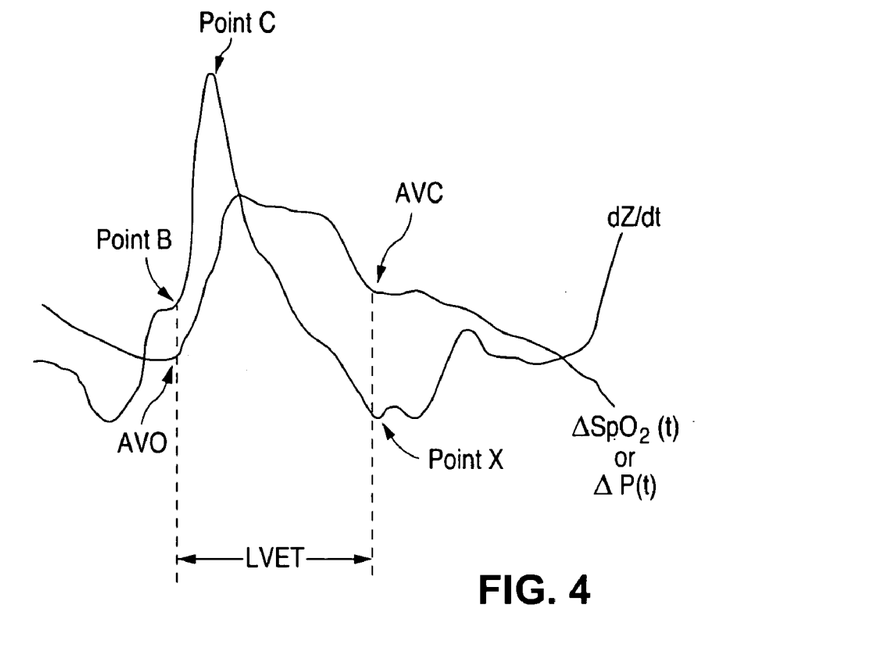
FIG. 4 shows the primary waveforms of $\Delta SpO_2(t)$ and/or $\Delta P(t)$, aligned in time with the $dZ/dt$ waveform.
Figure 5:
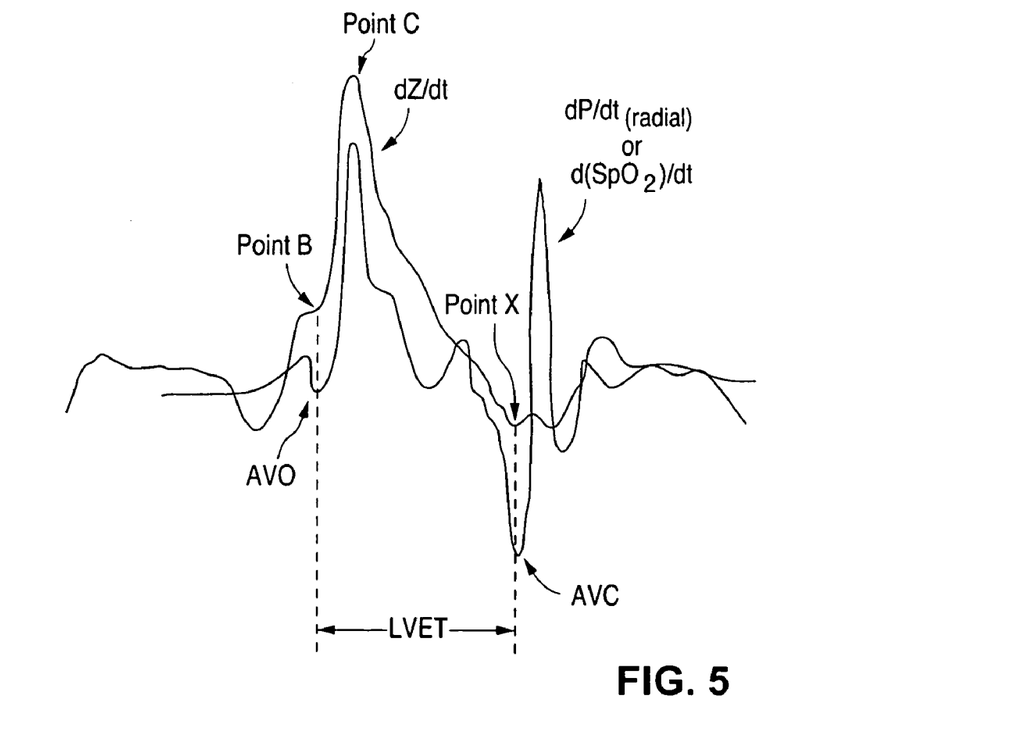
FIG. 5 shows an example where points B and X are distinguishable and that point B corresponds with aortic valve opening (AVO) on the first time-derivatives of either the $\Delta SpO_2(t)$ or $\Delta P(t)$ waveforms and point X corresponds with aortic valve closing (AVC) of either derivative.

Point B on the transbrachial $dZ/dt$ waveform is known to coincide with aortic valve opening, albeit with a time delay. Exemplary $dZ/dt$ waveforms demonstrate a distinct change in slope at, or not uncommonly above the zero baseline impedance, followed by a steep, positive linear segment ending at point C, or $dZ/dt_{max}$. When a distinct change in slope leading to point C is detected at or above the baseline, one skilled in the art of curve analysis can readily identify point B. However, as demonstrated by Debski TT et al. (Biol Psychol 1993; 36:63-74) using the transthoracic method, despite using fiducial landmarks on the time-derivatives of $dZ/dt$ (i.e. $d^2Z/dt^2$ and $d^3Z/dt^3$) to identify this change in slope, detection of point B can be problematic. This inability to correctly identify point B is obvious to those skilled in the art of curve analysis, and especially curve analysis of $dZ/dt$, by inspection of FIG. 3b. The method disclosed herein provides a new and innovative solution for point B detection. The new method employs one, or a combination of methods disclosed under determination of LVET; namely, $\Delta SpO_2(t)$ and/or $\Delta P(t)_{(radial)}$ (as shown in FIG. 4), or, respectively, their time derivatives, $d(SpO_2)/dt$ and/or $dP/dt_{(radial)}$ (as shown in FIG. 5). The technique of point B detection, as disclosed herein as a preferred embodiment, involves computerized curve fitting and alignment in time of temporal landmark X on the transbrachial dZ/dt curve with the dicrotic notch equivalent of one or both of the measured aforementioned oximetry and pressure curves, and/or preferably with one or both of their first time-derivatives. Independently, or in concert, one or both of the first time-derivative curves can be aligned in time with the transbrachial dZ/dt curve, such that the temporal point of the termination of flow, or aortic valve closure (AVC) equivalent on the first derivative oximetry or pressure curves, can be aligned in time with point X of the transbrachial dZ/dt curve. Point B, coinciding with aortic valve opening (AVO), and the beginning of flow, albeit with a time delay, is identified by determining the temporal point on the transbrachial dZ/dt curve, intersecting, and coinciding in time with the point of onset of flow/pressure on the $\Delta SpO_2(t)/\Delta P(t)$ curves, and/or on their first time-derivatives. This temporal point is identified as a discreet point at the baseline occurring before the first positive maximum upslope measured from foot of the respective baselines of the $\Delta SpO_2(t)$ and/or $\Delta P(t)_{(radial)}$ curves, and/or from their first time-derivatives (FIGS. 3a, 3b, 4, 5, 6).

Figure 6:
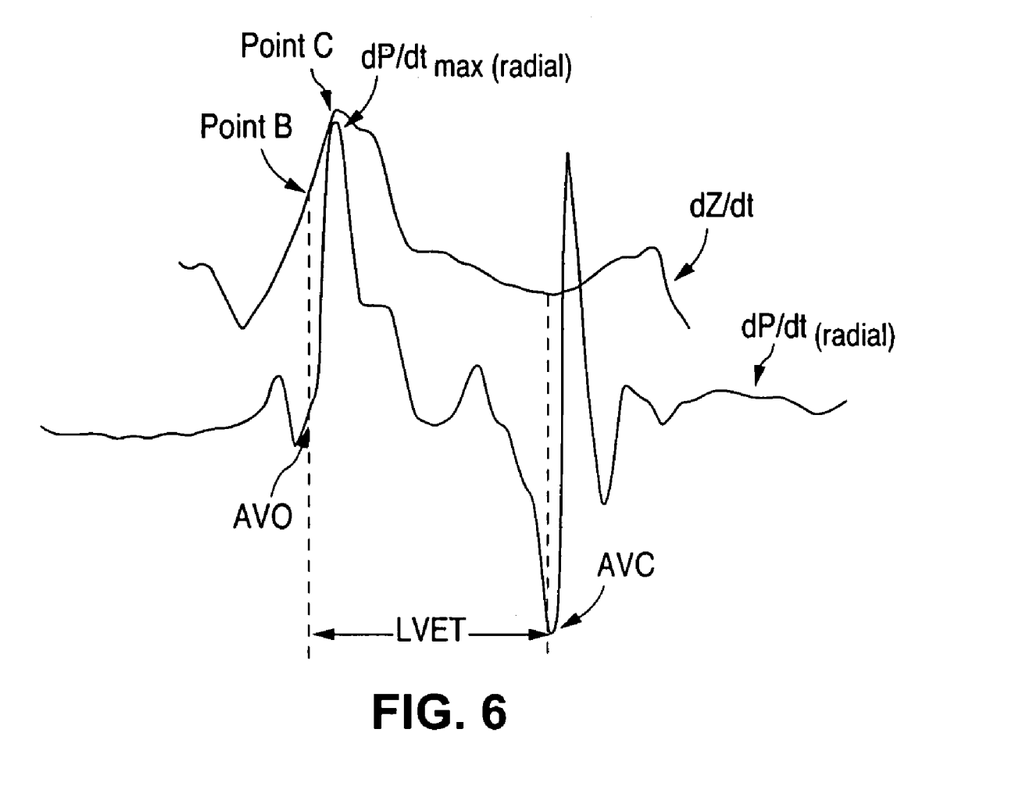
FIG. 6 shows a $dZ/dt$ waveform where points B and X are not distinguishable, and where point C ($dZ/dt_{max}$) is aligned in time with $dP/dt_{max(radial)}$.

2. Method for determining point B when point X is not readily identifiable by one skilled in the art of curve analysis (see FIG. 6):

When point X is not readily identifiable by one skilled in the art of curve analysis, then alternative means must be applied. Requiring alternative means, for example, would be the inability to identify the first zero crossing at baseline impedance after the zero crossing of point C ($dZ/dt_{max}$) on the second time-derivative curve of $\Delta Z(t)$(i.e., $d^2Z/dt^2$), where said zero crossing corresponds in time to point X and AVC. Said alternative means requires application of the first time-derivative of the applanation tonometry curve, $dP/dt_{(radial)}$ (FIG. 6). For one skilled in the art of curve analysis, said means requires alignment in time of the earliest maximum positive peak of dP/dt ($dP/dt_{max}$) with point C of the transbrachial dZ/dt curve. With point $dP/dt_{max}$ and point C aligned in time, point B can be identified by applying a perpendicular through, and coinciding in time with the onset at baseline of the first positive deflection of dP/dt, where said perpendicular line must intersect the dZ/dt curve at or above baseline impedance. The point of intersection of the perpendicular with the transbrachial dZ/dt curve is designated point B. When the above methods are unavailable, or fail to supply waveforms with fiducial landmarks necessary for point B detection, as assessed by pre-determined criteria, then, as default methods, a point on the transbrachial dZ/dt curve occurring 55 ms prior to point C, but obligatorily at or above baseline impedance, or alternatively, a point 15% above baseline impedance on the dZ/dt curve, is taken as point B.

Method for determining the maximum systolic upslope of transbrachial $\Delta Z(t)$, otherwise known as transbrachial $dZ/dt_{max}$: Employing one or a combination of the techniques described herein for point B detection, transbrachial $dZ/dt_{max}$ is the measured magnitude from point B to the maximum positive deflection of dZ/dt, which is $dZ/dt_{max}$, or point C, as shown in FIG. 2. $dZ/dt_{max}$ is a measured magnitude given in $\Omega/s^2$, and, whereas at point B, $dZ/dt=0$ ($\Omega/s^2$), $dZ/dt_{max} >> 0$ ($\Omega/s^2$).

In one embodiment, external calibration of the SV/CO by means of the transbrachial approach:

1. External calibration of $V_{c(brachium)}$ by means of the transthoracic method: Determination of $V_{c(cal)}$.

Because of the high correlation of $dV/dt_{max}$ measured in the aorta with that of the brachial artery, it is claimed that:

$$V_{c(thorax)} \cdot \sqrt{[(dZ/dt_{max})/Z_0]_{(thorax)}} \cdot T_{lve} = V_{c(brachium)} \cdot \sqrt{[(dZ/dt_{max})/Z_0]_{(brachium)}} \cdot T_{lve} \quad \text{equation 3}$$

Since $T_{lve}$ is equivalent for both sides of equation 3, $V_{c(brachium)}$ can be found thusly, $$V_{c(cal)} = V_{c(brachium)} = (V_{c(thorax)} \cdot \sqrt{[(dZ/dt_{max})/Z_0]_{(thorax)}})/(\sqrt{[(dZ/dt_{max})/Z_0]_{(brachium)}}) \quad \text{equation 4}$$

Where $V_{c(thorax)} = C_0 [W(kg) \cdot C_2]$     equation 5

Where $0.10 \leq C_0 < 0.5$, wherein $C_0 = 0.25$ in the preferred embodiment,

Thus, SV by the transbrachial method, externally calibrated from the transthoracic approach is given as, $$SV(\text{transbrachial}) = V_{c(cal)} \sqrt{[(dZ/dt_{max})/Z_0]_{(transbrachial)}} \cdot T_{lve} \quad \text{equation 6}$$

2. Determination of SV from the transbrachial approach by means of auto-calibration: A priori determination of $C_1$ as a mean value for a population, n.

In order to satisfy the requirements of equation 3, $V_{c(brachium)}$ is found by determining $V_{c(cal)}$ from the solution of equation 4. This operation requires insertion of $V_{c(thorax)}$ as determined from equation 5. Therefore, $V_{c(cal)}$ in equation 4 can be determined thusly;

$$V_{c(cal)} = C_1 \cdot [W(kg) \cdot C_2] \quad \text{equation 7}$$

Where, $C_1$ is thus, $$C_1 = V_{c(cal)}/[W(kg) \cdot C_2] \quad \text{equation 8}$$

where, $0 \leq C_1 < 50,000$, wherein the preferred embodiment $C_1$ is proprietary.

By solving equation 8 for a population, n, determining $V_{c(cal)}$ from equation 4, the mean value of the constant, $C_1$, can be found for the general population as follows;

$$C_1(\text{mean}) = [(C_{1-1} + C_{1-2} + C_{1-4} + \ldots C_{1-n})/n] \quad \text{equation 9}$$

Where $C_{1(mean)}$ ideally$=C_{1-1}$ through $C_{1-n}$. Thus,

SV determination by the transbrachial approach by auto-calibration is given as, $$SV(\text{transbrachial}) = (C_{1(mean)}[W(kg) \cdot C_2]) \cdot \sqrt{[(dZ/dt_{max})/Z_0]_{(transbrachial)}} \cdot T_{lve} \quad \text{equation 10}$$

What is claimed is:

1. An apparatus for determining stroke volume by bio-impedance from a patient's brachial artery, comprising:

two or more spaced apart alternating current flow electrodes positioned on the patient's arm proximate the brachial artery;

two or more spaced apart voltage sensing electrodes positioned on the patient's arm proximate the brachial artery, the voltage sensing electrodes being positioned between the alternating current flow electrodes;

an alternating current source electrically connected to the alternating current flow electrodes,     a voltmeter electrically connected to the voltage sensing electrodes;

a data input device;

a processing unit in communication with the data input device, the alternating current source, alternating current flow electrodes, the voltmeter, and voltage sensing electrodes, the processing unit capable of using data from the data input device and voltage sensing electrodes to calculate the stroke volume of the patient;

wherein the processing unit uses the equation:

$$SV_{(brachium)} = V_{c(brachium)} \cdot \sqrt{[(dZ/dt_{max})/Z_0]_{(brachium)}} \cdot T_{lve}$$

to determine stroke volume;

wherein $V_{c(brachium)}$ is determined by a calibration factor, $V_{c(cal)}$, using the equation:

$$V_{c(brachium)} = V_{c(cal)} = (V_{c(thorax)} \cdot \sqrt{[(dZ/dt_{max})/Z_0]_{(thorax)}})/(\sqrt{[(dZ/dt_{max})/Z_0]_{(brachium)}}),$$

and wherein the stroke volume equation is:

$$SV_{(brachium)} = V_{c(cal)} \cdot \sqrt{[(dZ/dt_{max})/Z_0]_{(brachium)}} \cdot T_{lve}.$$

2. An apparatus for determining stroke volume by bioimpedance from a patient's brachial artery, comprising:

two or more spaced apart alternating current flow electrodes positioned on the patient's arm proximate the brachial artery;

two or more spaced apart voltage sensing electrodes positioned on the patient's arm proximate the brachial artery, the voltage sensing electrodes being positioned between the alternating current flow electrodes;

an alternating current source electrically connected to the alternating current flow electrodes, a voltmeter electrically connected to the voltage sensing electrodes;

a data input device; and a processing unit in communication with the data input device, the alternating current source, alternating current flow electrodes, the voltmeter, and voltage sensing electrodes, the processing unit capable of using data from the data input device and voltage sensing electrodes to determine a peak rate of change of a measured cardiogenically induced transbrachial impedance variation and a left ventricular ejection time and to calculate the stroke volume of the patient therefrom;

wherein the processing unit uses the equation:

$$SV_{(brachium)} = V_{c(brachium)} \cdot \sqrt{[(dZ/dt_{max})/Z_0]_{(brachium)}} \cdot T_{lve}$$ to determine stroke volume, and wherein $T_{lve}$ is obtained from a dZ/dt waveform.

3. The apparatus of claim 2, wherein a trigger for initiating processing of the transbrachial dZ/dt waveform is obtained from an R wave of an antecedent ECG waveform.

4. The apparatus of claim 2, wherein a trigger for initiating processing of the transbrachial dZ/dt waveform is obtained from a C wave of an antecedent dZ/dt waveform.

5. An apparatus for determining stroke volume by bioimpedance from a patient's brachial artery, comprising:

two or more spaced apart alternating current flow electrodes positionable on the patient's arm proximate the brachial artery;

two or more spaced apart voltage sensing electrodes positionable on the patient's arm proximate the brachial artery, the voltage sensing electrodes being positionable between the alternating current flow electrodes;

an alternating current source electrically connected to the alternating current flow electrodes, a voltmeter electrically connected to the voltage sensing electrodes;

a data input device; and a processing unit in communication with the data input device, the alternating current source, the alternating current flow electrodes, the voltmeter, and the voltage sensing electrodes, wherein the processing unit is capable of using data from the data input device and a voltage sensed by the voltage sensing electrodes to calculate the stroke volume of the patient;

wherein the processing unit uses the equation:

$$SV_{(brachium)} = V_{c(brachium)} \cdot \sqrt{[(dZ/dt_{max})/Z_0]_{(brachium)}} \cdot T_{lve}$$

to calculate the stroke volume, where $SV_{(brachium)}$ is the stroke volume, $V_{(brachium)}$ is a volume of electrically participating brachial tissue, $dZ/dt_{max}$ is a peak rate of change of a measured cardiogenically induced transbrachial impedance variation, $Z_0$ is a quasi-static transbrachial base impedance, and $T_{lve}$ is a left ventricular ejection time; and wherein $V_{c(brachium)}$ is determined by a calibration factor, $V_{c(cal)}$, using the equation:

$$V_{c(brachium)} = V_{c(cal)} = (V_{c(thorax)} \cdot \sqrt{[(dZ/dt_{max})/Z_0]_{(thorax)}})/(\sqrt{[(dZ/dt_{max})/Z_0]_{(brachium)}}),$$

and wherein the stroke volume equation is:

$$SV_{(brachium)} = V_{c(cal)} \cdot \sqrt{[(dZ/dt_{max})/Z_0]_{(brachium)}} \cdot T_{lve}.$$

6. An apparatus for determining stroke volume by bioimpedance from a patient's brachial artery, comprising:

two or more spaced apart alternating current flow electrodes positionable on the patient's arm proximate the brachial artery;

two or more spaced apart voltage sensing electrodes positionable on the patient's arm proximate the brachial artery, the voltage sensing electrodes being positionable between the alternating current flow electrodes;

an alternating current source electrically connected to the alternating current flow electrodes, a voltmeter electrically connected to the voltage sensing electrodes;

a data input device; and a processing unit in communication with the data input device, the alternating current source, the alternating current flow electrodes, the voltmeter, and the voltage sensing electrodes, wherein the processing unit is capable of using data from the data input device and a voltage sensed by the voltage sensing electrodes to determine a peak rate of change of a measured cardiogenically induced transbrachial impedance variation and a left ventricular ejection time and to calculate the stroke volume of the patient therefrom;

wherein the processing unit uses the equation:

$$SV_{(brachium)} = V_{c(brachium)} \cdot \sqrt{[(dZ/dt_{max})/Z_0]_{(brachium)}} \cdot T_{lve}$$

to calculate the stroke volume, where $SV_{(brachium)}$ is the stroke volume, $V_{c(brachium)}$ is a volume of electrically participating brachial tissue, $dZ/dt_{max}$ is a peak rate of change of a measured cardiogenically induced transbrachial impedance variation, $Z_0$ is a quasi-static transbrachial base impedance, and $T_{lve}$ is a left ventricular ejection time, and wherein $T_{lve}$ is obtained from a dZ/dt waveform.

7. The apparatus of claim 6, wherein a trigger for initiating processing of the transbrachial dZ/dt waveform is obtained from an R wave of an antecedent ECG waveform.

8. The apparatus of claim 6, wherein a trigger for initiating processing of the transbrachial dZ/dt waveform is obtained from a C wave of an antecedent dZ/dt waveform.

* * * * *

UNITED STATES PATENT AND TRADEMARK OFFICE
CERTIFICATE OF CORRECTION

PATENT NO. : 7,261,697 B2
APPLICATION NO. : 10/870281
DATED : August 28, 2007
INVENTOR(S) : Donald P. Bernstein It is certified that error appears in the above-identified patent and that said Letters Patent is hereby corrected as shown below:

On the title page items:
(12) "Berstein" should read -- Bernstein --
(76) Inventor: "Donald P. Berstein" should read -- Donald P. Bernstein --

Signed and Sealed this

Twentieth Day of November, 2007

JON W. DUDAS
*Director of the United States Patent and Trademark Office*